United States Patent [19]
Schill et al.

[11] Patent Number: 5,807,737
[45] Date of Patent: Sep. 15, 1998

[54] HEART AND LUNG SUPPORT ASSEMBLY

[75] Inventors: David M. Schill, Knoxville, Tenn.; Joseph G. Schill, Lynchburg, Va.; Robert A. Schill, Jr., Henderson, Nev.

[73] Assignee: Schill Enterprises, Inc., Knoxville, Tenn.

[21] Appl. No.: 687,807

[22] Filed: Jul. 26, 1996

[51] Int. Cl.[6] .................................................. A01N 1/02
[52] U.S. Cl. .................. 435/284.1; 435/1.2; 435/286.5; 435/286.6
[58] Field of Search .................................. 435/1.2, 284.1, 435/286.5, 286.6; 128/202.12; 601/41, 43, 44

[56] References Cited

U.S. PATENT DOCUMENTS

| | | | |
|---|---|---|---|
| 2,195,744 | 4/1940 | Emerson | 601/43 |
| 4,756,705 | 7/1988 | Beijbom et al. | 604/4 |
| 4,770,165 | 9/1988 | Hayek | 128/202.12 |
| 5,051,352 | 9/1991 | Martindale et al. | 435/1.2 |
| 5,308,314 | 5/1994 | Fukui et al. | 604/4 |
| 5,308,320 | 5/1994 | Safar et al. | 604/4 |
| 5,385,540 | 1/1995 | Abbott et al. | 604/4 |
| 5,411,705 | 5/1995 | Thor et al. | 422/45 |
| 5,449,342 | 9/1995 | Hirose et al. | 604/4 |

FOREIGN PATENT DOCUMENTS

| | | | |
|---|---|---|---|
| 0 376 763 | 7/1990 | European Pat. Off. . | |
| 2004971 | 5/1983 | German Dem. Rep. | 435/284.1 |
| 288870 | 12/1970 | U.S.S.R. | 435/284.1 |

OTHER PUBLICATIONS

Chien et al "A simple technique for multiorgan preservation." J. Thorac. Cardiovasc. Surg. vol. 95 (1988), pp. 55–61.

Primary Examiner—William H. Beisner
Attorney, Agent, or Firm—Pitts & Brittian, P.C.

[57] ABSTRACT

A heart and lung support assembly for extracorporeal support of a heart and one or both associated lungs, using the lungs of the donor as oxygenators. The heart and lung support assembly is controlled by an automated feedback control system to monitor and control various attributes of the heart, lungs, and blood, such that the heart and lungs may be stabilized for an extended period of time in an extracorporeal state. The heart and lung support assembly includes generally a housing, a chest cavity actuator assembly, a blood pressure controller assembly, and an automated monitor and feedback control system. The housing is provided for receiving the heart, lungs, and trachea after being removed from the donor patient as a unit. The chest cavity actuator assembly is carried on the exterior of the housing and is provided for simulating normal inhaling and exhaling by the donor lungs. The blood pressure controller assembly is carried by the housing and includes a fluid circuit for the circulation of blood through the heart and lungs to simulate the normal circulation of blood and to provide a means for monitoring the composition and controlling the flow of the blood. The automated monitor and feedback control system includes an arterial cell for detecting at least the partial pressure of oxygen, the partial pressure of carbon dioxide, and pH levels in blood as the blood passes therethrough. A plurality of blood pressure detectors is provided for measuring the various pressures of interest.

20 Claims, 5 Drawing Sheets

HEART AND LUNG SUPPORT ASSEMBLY

TECHNICAL FIELD

This invention relates to the field of human and animal organ transplant devices. More specifically, the present invention is directed to a device for sustaining the life of a heart and one or both lungs associated with the heart after being removed from a donor and prior to being implanted into a recipient, the heart and lungs being maintained at approximate corporeal conditions while extracorporeal. The device uses the donor's lungs for extracorporeal oxygenation of blood used to maintain the normal functions of the heart.

BACKGROUND ART

In the field of organ transplant, and specifically heart transplant, it is well known that the time between harvesting a heart from a donor and implanting the heart into a recipient patient is critical. It is unusual that the donor and recipient patients are closely located with respect to each other, thus requiring emergency transport of the heart. Conventionally, the heart is placed on ice in a cooler and rushed to the recipient site. However, there is typically only a few hours within which a successful transplant may be made.

There are several devices which have been developed for use in surgery such as open heart surgery, for treating blood, or for assisting in the circulation of blood. Typical of the art are those devices disclosed in the following U.S. Patents:

| U.S. Pat. No. | Inventor(s) | Issue Date |
| --- | --- | --- |
| 4,756,705 | P. Beijbom, et al. | July 12, 1988 |
| 5,308,314 | Y. Fukui, et al. | May 3, 1994 |
| 5,308,320 | P. Safar, et al. | May 3, 1994 |
| 5,385,540 | M. S. Abbott, et al. | Jan. 31, 1995 |
| 5,411,705 | E. J. Thor, et al. | May 2, 1995 |
| 5,449,342 | T. Hirose, et al. | Sep. 12, 1995 |

Of these patents, those issued to Fukui, et al. ('314), Safar, et al. ('320), Abbott, et al. ('540), and Thor, et al. ('1,705), each disclose a device for treating blood for various purposes. For example, the '320 device is provided for withdrawing blood from a patient, oxygenating the blood, and returning it to the patient. The '540 device is provided for delivering cardioplegic solution to the heart during open heart surgery. The '1,705 device is also provided for the extracorporeal treatment of blood during open-heart surgery. However, neither of these devices is provided for assisting in the sustenance of life of a heart during transplant. Further, neither of these devices discloses a means for controlling the function of the lungs for oxygenation of blood used to sustain the life of the heart.

The '342 device disclosed by Hirose, et al, is provided for assisting in the circulation of blood. The '342 device also serves to replace carbon dioxide in the blood with oxygen. The '342 device is thus provided for assisting the functions of the lung in order to reduce the load on the heart and increase the blood flow volume of the coronary artery. As in the previously discussed devices, the '342 device is not provided for sustaining the life of a heart during transplant thereof Moreover, the '342 device is not provided for the extracorporeal control of the donor's lungs in order to oxygenate blood flowing through the heart being transplanted.

The '6,705 device disclosed by Beijbom, et al., is similar to ones mentioned above, with the noted distinction that Beijbom, et al., disclose the use of the patient's lungs for oxygenation of the blood during heart surgery. However, although the blood is extracorporeal during oxygenation thereof, the device is used specifically during heart surgery. The '6,705 device is not provided for sustaining the life of a heart during transplant, nor for controlling the functions of the lungs to accomplish oxygenation of the blood.

Therefore, it is an object of this invention to provide a means for sustaining the life of a human or animal heart and lungs after removal from a donor patient and until implanting the heart into a recipient patient.

A further object of the present invention is to provide such a device whereby the donor's lungs and trachea are also removed and used for oxygenating blood used in sustaining the life of the heart.

Another object of the present invention is to provide such a device whereby the heart and lungs are maintained in an environment approximating the normal corporeal conditions of the heart and lungs for extended periods of time.

DISCLOSURE OF THE INVENTION

Other objects and advantages will be accomplished by the present invention which is provided for extracorporeal support of a heart and associated pair of lungs between the time the heart and lungs are removed from a donor and implanted into a recipient. Moreover, in the preferred embodiment the heart and lung support assembly is designed to use the lungs of the donor as oxygenators for the heart during the extracorporeal support thereof The heart and lung support assembly is controlled by an automated system to monitor and control various attributes of the heart, lungs, and blood, such that the heart may be stabilized for an extended period of time in an extracorporeal state. The heart and lung support assembly is comprised generally of a housing, a chest cavity actuator assembly, a blood pressure controller assembly, and an automated monitor and feedback control system. The housing is provided for receiving the heart, lungs and trachea after being removed from the donor patient. The housing is pressure controlled such that the chest cavity actuator assembly may effectively draw ambient air into the lungs for oxygenation of the blood, and to expel carbon dioxide therefrom. Defibrillator pads are carried by the housing for applying an electrical charge to the heart.

The chest cavity actuator assembly is carried on the exterior of the housing and includes an elastomeric membrane secured to the housing such that an air inductor opening defined by the housing is covered. A support bracket is provided for carrying a servo motor. A piston-type actuator is carried by the servo motor, the second end of which is secured to a central portion of the membrane. The servo motor is controlled to reciprocate the actuator second end away from and toward the housing. As the actuator second end is pulled away from the housing, a vacuum is created in the housing, thus causing ambient air to be drawn into the lungs through the trachea. As the actuator second end is pushed toward the housing, air within the lungs is expelled through the trachea.

The blood pressure controller is carried by the housing and includes a fluid circuit for the circulation of blood through the heart and lungs to simulate the normal circulation of blood and to provide a means for monitoring the composition and controlling the flow of the blood. The fluid circuit generally includes a simulated aorta, an external conduit, and a simulated vena cava. The simulated vena cava includes a simulated superior vena cava and a simulated inferior vena cava. The external conduit includes a flexible tubing section. In order to control the blood pressure, the blood pressure controller includes a reciprocating piston driven by a servo motor. The distal end of the reciprocating piston is disposed in contact with the flexible tubing section of the fluid circuit. The distal end of the reciprocating piston is moved toward or away from the center of the flexible tubing in order to decrease or increase the cross-sectional area of the inside of the flexible tubing, thereby changing the blood pressure.

The automated monitor and feedback control system includes an arterial cell disposed in the fluid circuit between the blood outlet and the flexible tubing section. The arterial cell is provided for detecting at least the partial pressure of oxygen ($pO_2$), the partial pressure of carbon dioxide ($pCO_2$), and pH levels in blood as the blood passes therethrough. A controller is provided for controlling the operation of the chest cavity actuator assembly servo motor in response to the data collected by the comparator.

The automated monitor and feedback control system further includes a plurality of blood pressure detectors for measuring the various pressures of interest. Included are a central venous pressure (CVP) detector, a pulmonary artery pressure (PA) detector, a left auricle pressure (LA) detector, and an aortic pressure (ART) detector. A comparator is provided for comparing each of the measured values obtained by the CVP, PA, LA, and ART detectors to predetermined values to determine if any is out of range. The comparator then outputs results to a signal processor for determining whether the blood pressure controller assembly is operating at optimum. Output from the signal processor is output to a controller provided for controlling the blood pressure controller assembly.

A pacemaker is provided for maintaining the heart rate at a prescribed level. The pacemaker is of a conventional type provided with a dedicated feedback and control system for control thereof The pacemaker is provided for detecting a lower threshold heart rate such that when the heart rate falls below the threshold, the pacemaker will activate to cause the heart rate to increase. While feedback and control system associated with the pacemaker detects the heart rate to be above the threshold, the pacemaker remains inactive with respect to controlling the heart rate. The threshold level is adjustable such that various heart rates may be selected as the lower threshold. The primary function of the pacemaker is to be a safety precaution.

BRIEF DESCRIPTION OF THE DRAWINGS

The above mentioned features of the invention will become more clearly understood from the following detailed description of the invention read together with the drawings in which.

BEST MODE FOR CARRYING OUT THE INVENTION

A heart and lung support assembly incorporating various features of the present invention is illustrated generally at 10 in the figures. The heart and lung support assembly 10 is designed for extracorporeal support of a heart 132 and at least one associated lung 142 between the time the heart 132 and lungs 142 are removed from a donor and implanted into a recipient. Moreover, in the preferred embodiment the heart and lung support assembly 10 is designed to use the lungs 142 of the donor as oxygenators for the heart 132 during the extracorporeal support thereof. The heart and lung support assembly 10 is controlled by an automated system to monitor and control various attributes of the heart 132, lungs 142, and blood, such that the heart 132 may be stabilized for an extended period of time in an extracorporeal state, especially compared to prior art methods.

Figure 1:
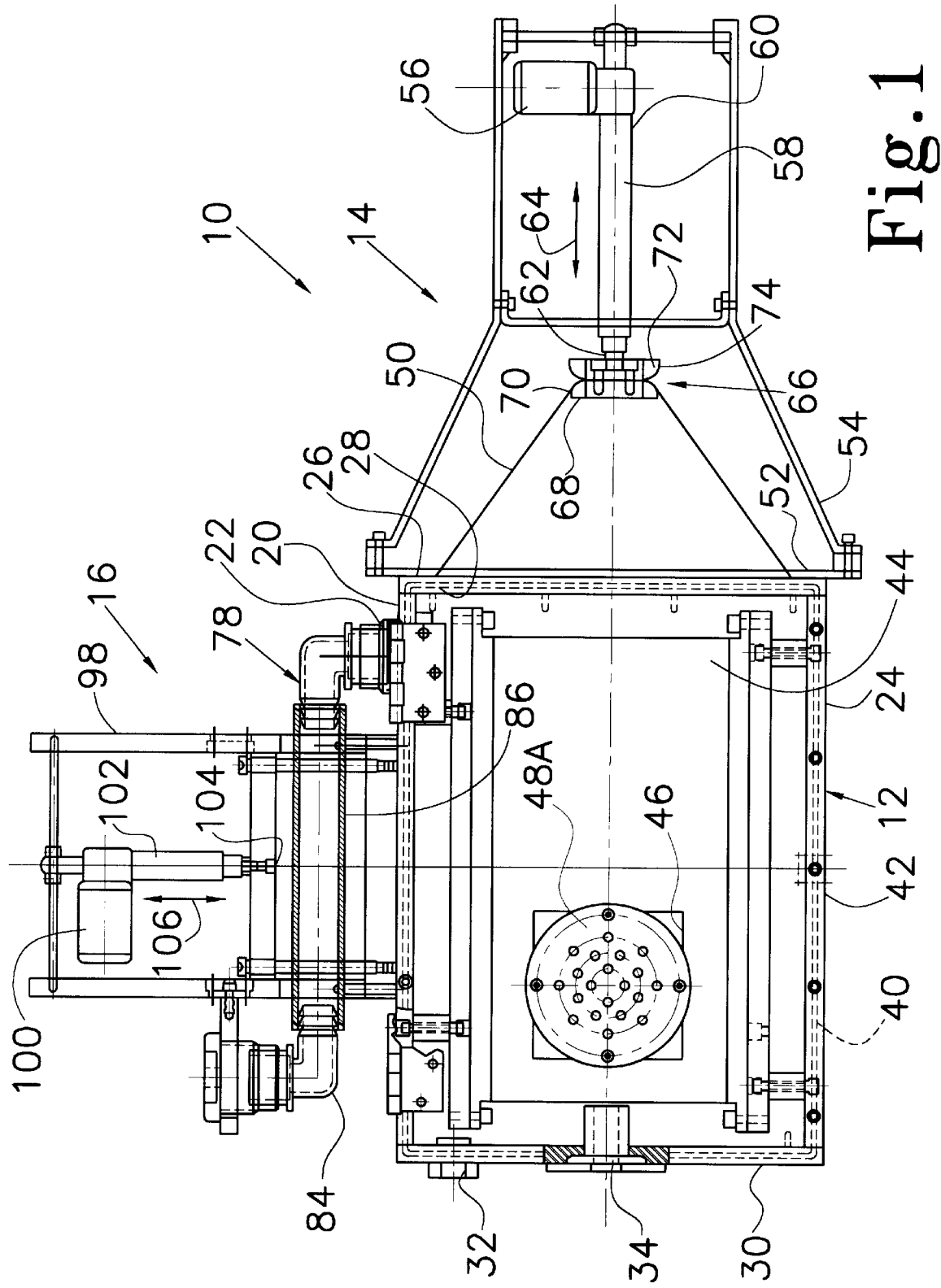
FIG. 1 is a top plan view of the heart and lung support assembly constructed in accordance with several features of the present invention.
Figure 3:
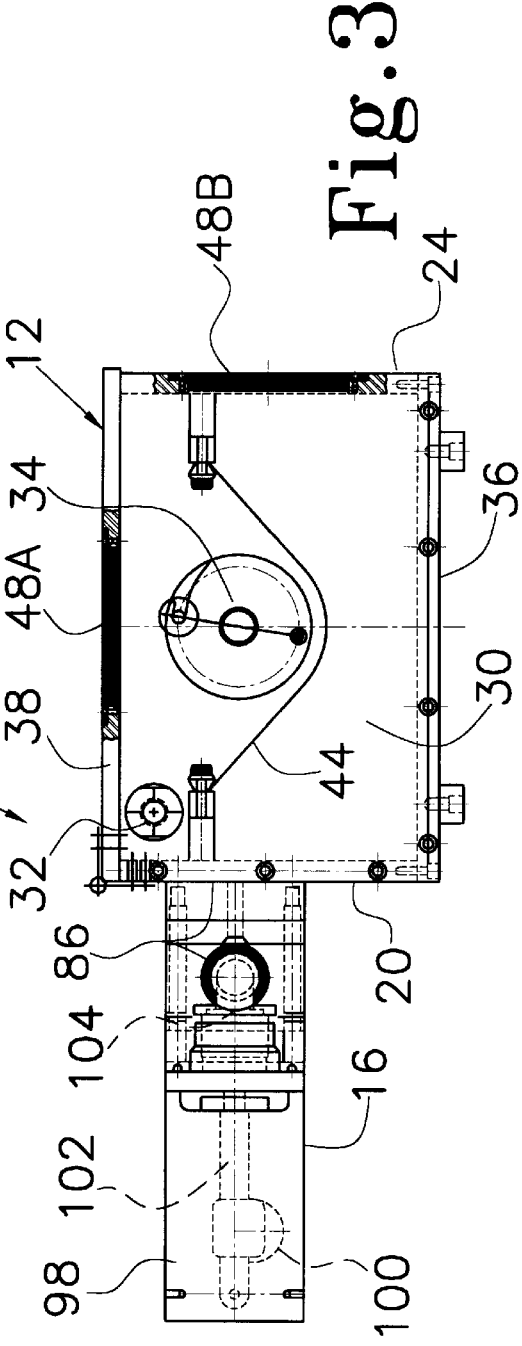
FIG. 3 is an end elevation view, partially in section, of the heart and lung support assembly illustrated in FIG. 1.
Figure 4:
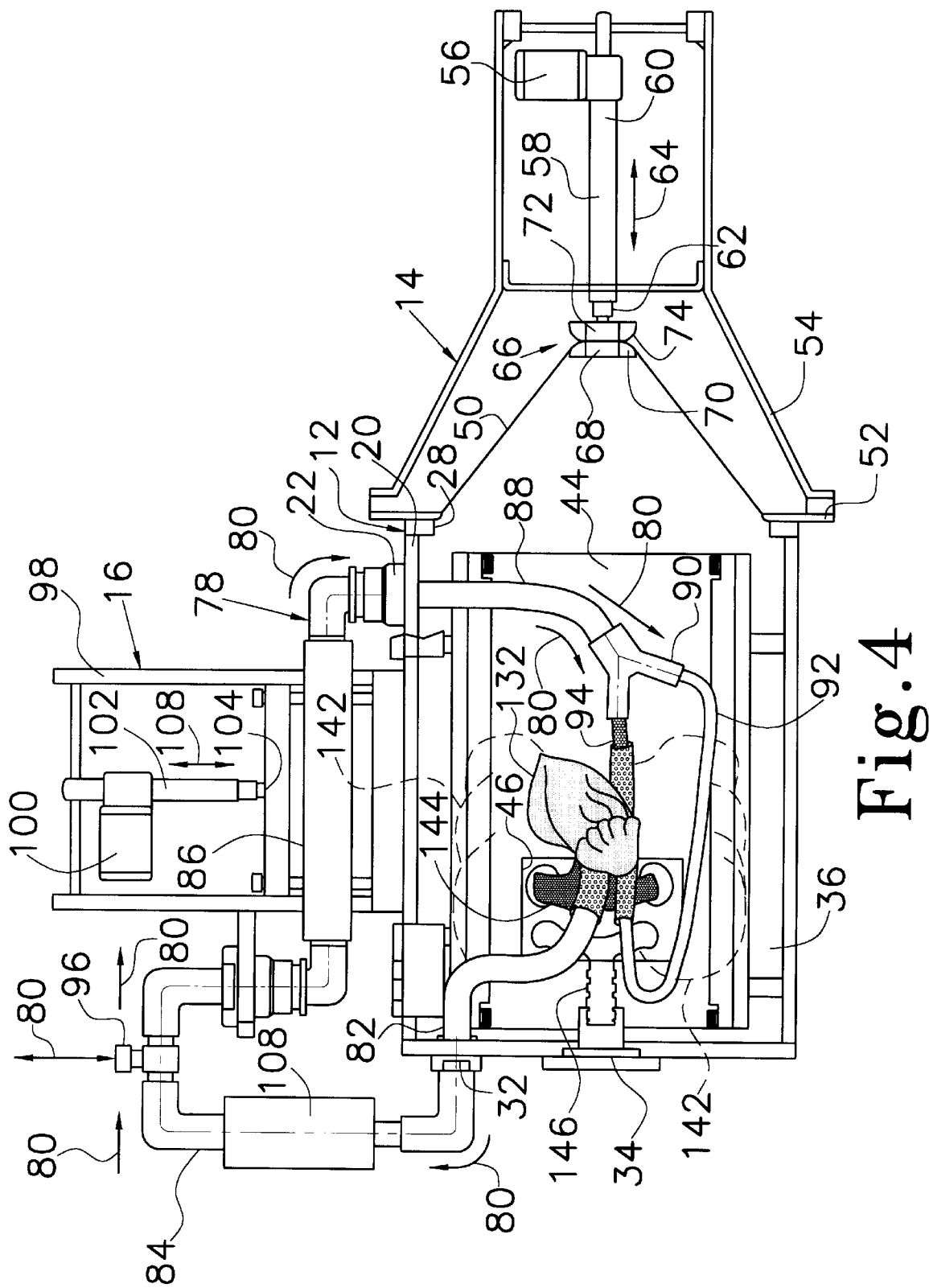
FIG. 4 illustrates a top plan view of the heart and lung support assembly illustrated in FIG. I wherein a heart and associated pair of lungs are shown being supported.

The heart and lung support assembly 10, as best illustrated in FIGS. 1 and 4, is comprised generally of a housing 12, a chest cavity actuator assembly 14, a blood pressure controller assembly 16, and an automated monitor and feedback control system 18. The housing 12 is provided for receiving the heart 132 and lungs 142 after being removed from the donor patient. As best illustrated in FIGS. 3 and 4, a cradle 44 is carried within the housing 12 for placement of the heart 132. As illustrated in FIG. 4, the cradle 44 defines a slotted opening 46 through which the pulmonary artery and vein 144 pass. While deflated, the lungs 142 are passed through the slotted opening 46 to the bottom 36 of the housing 12, and more specifically, under and on either side of the heart 132, in close approximation to the relative position of each within the human body. The pulmonary artery and vein 144 thus serve their natural function of communicating blood between the heart 132 and lungs 142. The slotted opening 46 is also provided for the passage of the trachea 146 from the lungs 142 to a trachea receptor 34 carried by the housing 12, as described below. The trachea 146 is thus allowed to operate in its natural manner to communicate air into and out of the lungs 142.

The housing 12 is pressure controlled such that the chest cavity actuator assembly 14, as described below, may effectively draw ambient air into the lungs 142 for oxygenation of the blood, and to expel carbon dioxide therefrom. The housing 12 is provided with a lid 38 hinged along one side to the first side wall 20 of the housing 12 for accessing the interior of the housing 12 for placement and removal of the heart 132 and lungs 142. A seal 40 is provided for accomplishing pressure control of the interior volume of the housing 12 and for preventing the entrance of foreign matter into the housing 12, thereby ensuring the viability of the heart 132. A closure device 42 is provided for selectively maintaining the hinged lid 38 in a closed fashion.

A first end wall 26 of the housing 12 defines an air inductor opening 28 to cooperate with the chest cavity actuator assembly 14, as described below. The housing 12 also defines a trachea receptor 34 in the second end wall 30 for the inlet of ambient air and the outlet of spent air. A blood outlet 32 and a blood inlet 22 are also defined by the housing 12 for the circulation of blood through the heart 132 and lungs 142, and further through the automated monitor and feedback control system 18. The blood outlet 32 is defined by the second end wall 30 and the blood inlet 22 is defined by the first side wall 20.

Defibrillator pads 48 are carried by the housing 12 for applying an electrical charge to the heart 132. As illustrated, a first defibrillator pad 48A is carried by the hinged lid 38 and a second defibrillator pad 48B is carried by the second side wall 24 of the housing 12.

The chest cavity actuator assembly 14 is carried on the exterior of the housing 12 on the first end wall 26 thereof. The chest cavity actuator assembly 14 includes an elastomeric membrane 50 secured to the first end wall 26 of the housing 12 on the exterior thereof such that the air inductor opening 28 is covered. To this extent, the membrane 50 is interposed between the housing first end wall 26 and a mounting frame 52. A support bracket 54 is carried by the mounting frame 52 for carrying a servo motor 56. The first end 60 of a piston-type actuator 58 is carried by the servo motor 56. The second end 62 of the actuator 58 is secured to a central portion of the membrane 50. As illustrated, the actuator second end 62 is secured to the membrane 50 by means of a mounting block 66. The mounting block 66 includes first and second halves 68,72 secured to each other, with one each being disposed on either side of the membrane 50. The perimeter of each half 68,72 of the mounting block 66 is curved on the respective engagement side 70,74 thereof in order to limit degradation of the membrane 50.

The servo motor 56 is controlled to reciprocate the actuator second end 62 away from and toward the housing 12, as indicated by the direction arrows 64. As the actuator second end 62 is pulled away from the housing 12, a vacuum is created in the housing 12, thus causing ambient air to be drawn into the lungs 142 through the trachea 146. As the actuator second end 62 is pushed toward the housing 12, air within the lungs 142 is expelled through the trachea 146. Therefore, the normal function of the lungs 142 is replicated by operation of the servo motor 56. As will be described below, the servo motor 56 is controllable to vary the length and rate of the stroke of the actuator 58 in order to control the oxygenation of blood. Although a preferred embodiment of the chest cavity actuator assembly 14 has been illustrated and described, it will be understood that other embodiments of a chest cavity actuator assembly 14 may be employed to accomplish the simulation of inhaling and exhaling by the lungs 142.

The blood pressure controller assembly 16 is carried by the first side wall 20 of the housing 12. As is best illustrated in FIG. 4, the blood pressure controller assembly 16 includes a fluid circuit 78 for the circulation of blood through the heart 132 and lungs 142, as indicated by the arrows 80, to simulate the normal circulation of blood and to provide a means for monitoring the composition and controlling the flow of the blood. The fluid circuit 78 generally includes a simulated aorta 82, an external conduit 84, and a simulated vena cava 88. The simulated vena cava 88 is provided with a connector 90 such that blood flow therethrough is divided to be delivered through a simulated superior vena cava 92 and a simulated inferior vena cava 94. The simulated aorta 82 is configured to extend between the left ventricle 136 (see FIG. 5) of the heart 132 to the blood outlet 32 defined by the housing second end wall 30. The external conduit 84 extends between the blood outlet 32 and the blood inlet 22 defined by the housing first side wall 20 and includes a flexible tubing section 86. The simulated vena cava 88 is configured to extend between the blood inlet 22 and the right auricle 138 (see FIG. 5) of the heart 132. Thus, the fluid circuit 78 simulates the circulatory system of the body from which the heart 132 and lungs 142 were removed.

Figure 6:
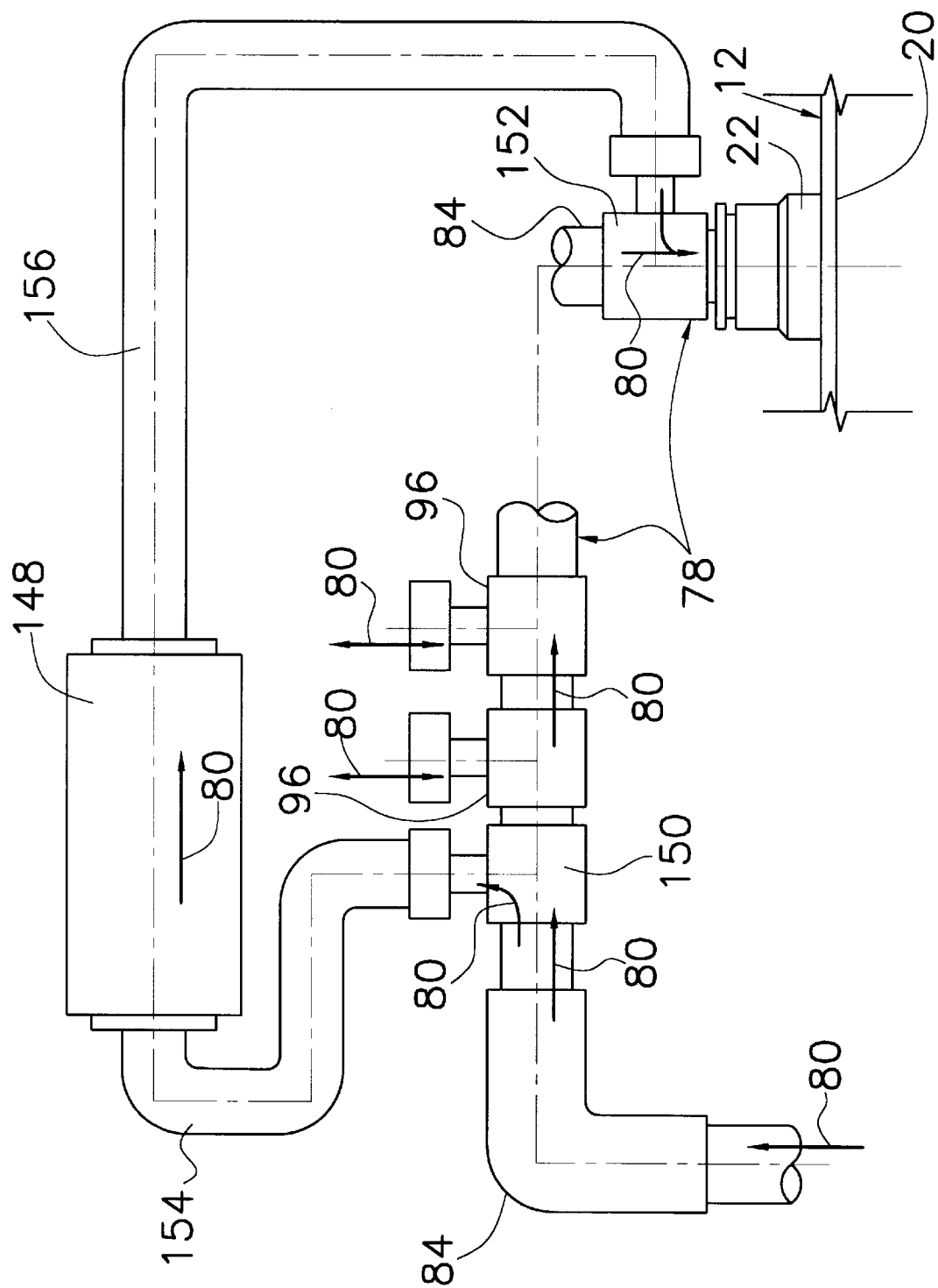
FIG. 6 illustrates a segment of the fluid circuit wherein a hemo filter is provided for filtering impurities from blood being circulated through the heart and lung support assembly of the present invention.

A fluid inlet/outlet 96 is provided in the external conduit 84 between an arterial cell 108 and the blood pressure control assembly 16, both described in greater detail below. The fluid inlet/outlet 96 is provided for either manually or automatically introducing fluids into the fluid circuit 78 after the heart 132, lungs 142 and trachea 146 have been placed within the housing 12 and attached to the heart and lung support assembly 10. The fluid inlet/outlet 96 may also be used to manually or automatically tap excess fluid from the fluid circuit 78 as required. The fluid inlet/outlet 96 of the preferred embodiment is of a conventional type, such as a Luer lock port. Other conventional devices may be incorporated as well. As illustrated in FIG. 6, more than one fluid inlet/outlet 96 may be provided.

As illustrated in FIG. 6, the fluid circuit 78 may also be provided with a hemo filter 148 for removing impurities from the blood being circulated through the heart and lung support assembly 10. The hemo filter 148 is disposed in parallel fashion to the fluid circuit 78 in a conventional manner. In the illustrated embodiment, an outlet 150 and an inlet 152 are each provided in the external conduit 84. The outlet 150 is disposed upstream from the fluid inlet/outlet 96 on the high pressure side of the heart 132. The inlet 152 is disposed on the low pressure side of the heart 132 immediately upstream from the blood inlet 22 defined on the housing first side wall 20. An inlet tubing is provided for fluid communication between the outlet 150 and the hemo filter 148. An outlet tubing 156 is provided for fluid communication between the hemo filter 148 and the inlet 152. The outlet 150 and inlet 152 are similar to the fluid inlet/outlet 96 described previously, and, to that extent, can be any conventional type of inlet/outlet. When the hemo filter 148 is used, a portion of the blood being circulated through the fluid circuit 78 is diverted through the outlet 150 and the inlet tubing 154 to the hemo filter 148, where impurities in the blood are removed. The blood is then delivered through the outlet tubing 156 and the inlet 152 where it is mixed with the remainder of the blood and then circulated through the remainder of the fluid circuit 78.

In order to control the blood pressure, the blood pressure controller assembly 16 includes a reciprocating piston 102 driven by a servo motor 100 as indicated by the direction arrows 106. The servo motor 100 is carried by a mounting bracket 98 which is mounted on the housing first side wall 20. The distal end 104 of the reciprocating piston 102 is disposed in contact with the flexible tubing section 86 of the fluid circuit 78. The distal end 104 of the reciprocating piston 102 is moved toward or away from the center of the flexible tubing section 86 in order to decrease or increase the cross-sectional area of the inside of the flexible tubing section 86, thereby changing the blood pressure. As the cross-sectional area of the flexible tubing section 86 is decreased, the arterial blood pressure is increased, and vice versa. Although a preferred embodiment of a blood pressure controller assembly 16 has been illustrated in described, it will be understood that other embodiments of a blood pressure controller assembly 16 may be equally effective to selectively raise and lower the blood pressure within the circulatory system, especially within the chambers of the heart 132.

Figure 5:
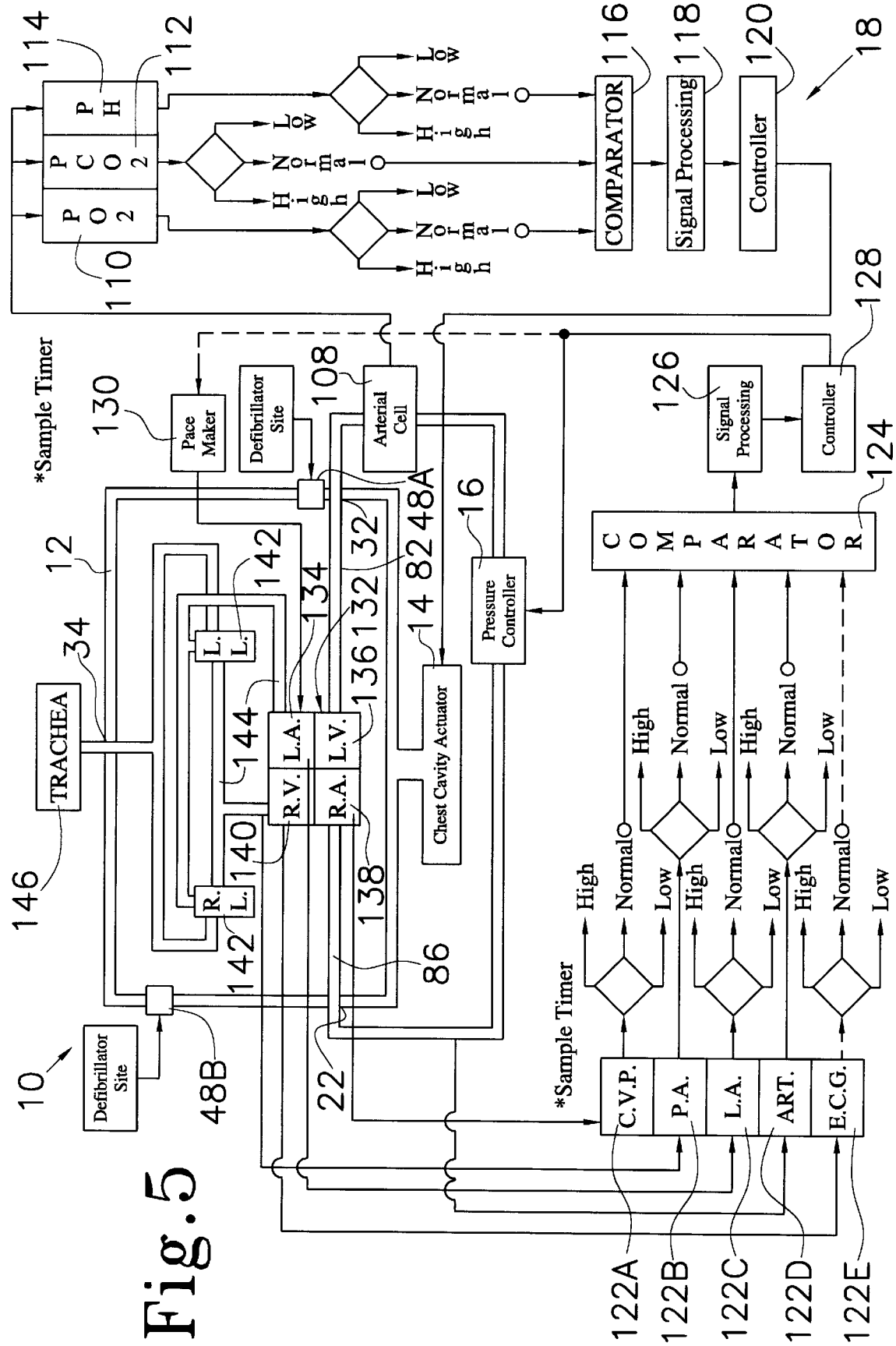
FIG. 5 is a schematic illustration of the heart and lung support assembly of the present invention graphically showing the functions of the automated monitor and feedback control system.

The automated monitor and feedback control system 18 includes an arterial cell 108 disposed in the fluid circuit 78 between the blood outlet 32 and the blood pressure controller assembly 16. The arterial cell 108 is provided for detecting at least the partial pressure of oxygen ($pO_2$) 110, the partial pressure of carbon dioxide ($pCO_2$) 112, and pH 114 levels in blood as the blood passes therethrough. As illustrated in FIG. 5, each attribute is detected as being low, normal, or high. The measured level of each is then compared by a comparator 116 to determine if either is out of an acceptable range. The results attained by the comparator 116 are processed by a signal processor 118, which then signals a controller 120. The controller 120 is provided for controlling the operation of the chest cavity actuator servo motor 56. For example, the comparator 116 may determine that the oxygen level in the blood is too low, thus resulting the signal processor 118 signaling to the controller 120 to increase the length or rate of the stroke in order to increase the volume or rate of air pulled into the lungs 142.

The automated monitor and feedback control system 18 further includes a plurality of blood pressure detectors 122 for measuring the various pressures of interest. Included are a central venous pressure (CVP) detector 122A, a pulmonary artery pressure (PA) detector 122B, a left auricle pressure (LA) detector 122C, and an aortic pressure (ART) detector 122D. The CVP detector 122A is provided for measuring the blood pressure in the right auricle 138, the low pressure side of the heart 132. The PA detector 122B is provided for measuring the pressure of the venous blood going into the lungs 142 from the right side of the heart 132. The LA detector 122C is provided for measuring the pressure in the left auricle 134 of the heart 132. The ART detector 122D is provided for measuring the pressure of blood leaving the heart 132 from the left ventricle 136, the high pressure side of the heart 132. The ART detector 122D measures the blood pressure between the simulated aorta 82 and the blood pressure controller assembly 16.

A comparator 124 is provided for comparing each of the measured values obtained by the CVP, PA, LA, and ART detectors 122A,B,C,D to predetermined values to determine if any is out of range. As illustrated in FIG. 5, each measured value is determined to be high, normal, or low. The comparator 124 then outputs results to a signal processor 126 for determining whether the blood pressure controller assembly 16 is operating at optimum. Output from the signal processor 126 is input to a controller 128 provided for controlling the blood pressure controller assembly 16. Specifically, the blood pressure controller assembly 16 adjusts the aortic blood pressure as described above in response to the controller 128 commands by adjusting the position of the piston 102 with respect to the flexible tubing section 86 of the fluid circuit 78.

As illustrated, a pacemaker 130 is provided for maintaining the heart rate at a prescribed level. The pacemaker 130 is of a conventional type provided with a dedicated feedback and control system (not illustrated) for control thereof The pacemaker 130 is provided for detecting a lower threshold heart rate such that when the heart rate falls below the threshold, the pacemaker 130 will activate to cause the heart rate to increase. While feedback and control system associated with the pacemaker 130 detects the heart rate to be above the threshold, the pacemaker 130 remains inactive with respect to controlling the heart rate. The threshold level is adjustable such that various heart rates may be selected as the lower threshold. The primary function of the pacemaker 130 is to be a safety precaution.

Alternatively, the pacemaker 130 may be of a type not having a dedicated feedback and control system. In this case, the automated monitor and feedback control system 18 is further provided with a heart rate detector 122E. The comparator 124 determines if the measured heart rate is out of range. The signal processor 126 then signals the controller 128 to control the pacemaker 130 accordingly.

Figure 2:
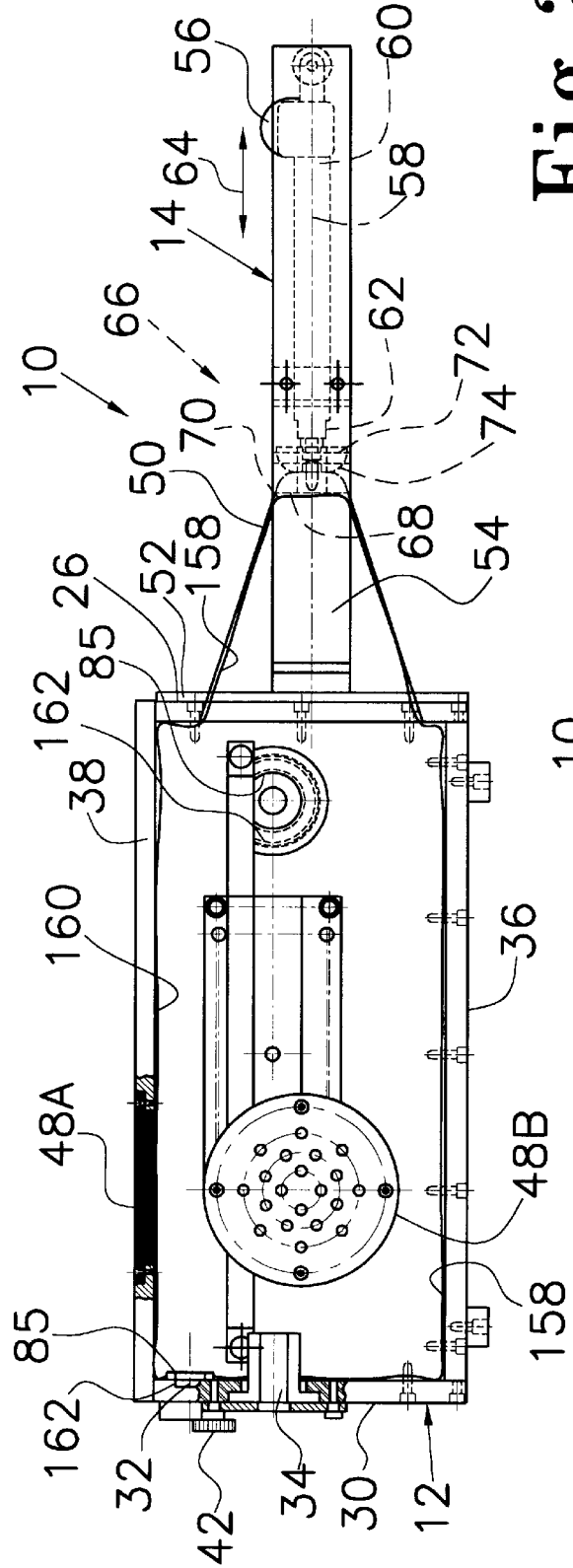
FIG. 2 is a side elevation view, partially in section, of the heart and lung support assembly illustrated in FIG. 1.

As illustrated in FIG. 2, it is envisioned that a housing liner 158 and a lid liner 160 may be provided for maintaining the sterility of the interior of the housing 12 from one use to the next. As illustrated, the housing liner 158 is configured to closely conform to the interior of the housing first and second side and end walls 20, 24, 26, 30 and the housing bottom wall 36. The housing liner 158 is configured at one end corresponding to the housing first end wall 26 to allow operation of the chest cavity actuator assembly 14 without jeopardizing the sterility of the housing 12. To this extent, the housing liner 158 is configured to closely assimilate the contour of the elastomeric membrane 50 at its farthest extent from the housing 12. The housing liner 158 is secured to the mounting block 66 in a conventional manner such as with releasable adhesives (not shown).

At the blood inlet and outlets 22, 32, and the trachea receptor 34, the housing liner 158 defines openings 162 corresponding thereto. To this extent, the trachea receptor 34 may be disposable. Further, the external conduit 84 of the fluid circuit 78 is provided with a fastener such as a nut 85 under which is received the housing liner 158. The lid liner 160 is secured to the perimeter of the lid 38 in a conventional manner such as with a releasable adhesive. After each use, the nuts 85, trachea receptor 34, housing liner 158 and lid liner 160 are removed.

The nuts 85 are then sterilized. The trachea receptor 34, housing liner 158 and lid liner 160 are each discarded and replaced.

As described, the heart and lung support assembly 10 is provided for extracorporeal support of a human or animal heart 132 and lungs 142 using the lungs 142 of the donor as an oxygenator for the heart 132. When a heart 132 is harvested from a donor and transplanted into a recipient, the lungs 142, the pulmonary artery and vein 144, and trachea 146 are also harvested as a unit, with each remaining intact with each other so that communicative functions between each may be maintained in a natural manner. The heart 132, lungs 142 and trachea 146 are positioned within and connected to the heart and lung support assembly 10 using the simulated circulatory and respiratory systems of the body. The chest cavity actuator assembly 14 is then activated to begin the simulated breathing of the lungs 142 such that blood being circulated through the heart 132, lungs 142, and heart and lung support assembly 10 is oxygenated. The arterial cell 108 is provided to periodically test the composition of the blood in order to provide data for controlling the chest cavity actuator assembly 14. The blood pressure controller assembly 16 is provided for maintaining the proper blood pressure within the entire circulatory system. The blood pressure detectors 122 periodically detect the various blood pressures within the system in order to determine when the blood pressure controller assembly 16 is to be adjusted.

From the foregoing description, it will be recognized by those skilled in the art that a heart and lung support assembly offering advantages over the prior art has been provided. Specifically, the heart and lung support assembly provides a means for the extracorporeal support of a human or animal heart using the lungs of the donor as an oxygenator. It is envisioned that, although the present invention is described as supporting the life of a heart, it is envisioned that the same technology may be adapted for the support of other organs harvested for transplant. It is also envisioned that the heart and lung support assembly of the present invention may be used to sustain the life of one or both of the lungs for transplant, using the heart to continuously cycle blood.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, We claim:

1. A heart and lung support assembly for extracorporeal support of a donor heart using the donor lungs as an oxygenator for blood being pumped therethrough by the donor heart, said heart and lung support assembly comprising:

a housing defining an enclosure for placement of a donor heart and donor lungs, said housing defining a trachea opening configured to mount a trachea receptor therein, said trachea receptor being configured for attachment of a trachea associated with the donor lungs thereto;

a cradle carried within said housing above a bottom of said housing for placement of the donor heart thereon, the donor lungs being positioned on said housing bottom below the donor heart, the donor lungs remaining intact with and in a normal disposition with the donor heart;

a chest cavity actuator assembly carried by said housing for inducing inhaling and exhaling of the donor lungs, said chest cavity actuator being operable to create a vacuum within said housing to induce a draw of air into the donor lungs;

a fluid circuit for circulating blood through the donor heart and donor lungs in similar fashion to the circulatory system associated with the donor heart;

a blood pressure controller assembly for selectively raising and lowering the pressure of blood being pumped through said heart and lung support assembly; and an automated monitor and feedback control system including a blood content detector for detecting levels of components in blood circulated through said heart and lung support assembly and at least one blood pressure detector for detecting at least one blood pressure associated with the donor heart, said automated monitor and feedback control system controlling said chest cavity actuator assembly and said blood pressure controller assembly as a result of data obtained from said blood content detector and said at least one blood pressure detector.

2. The heart and lung support assembly of claim 1 wherein said chest cavity actuator assembly includes an elastomeric membrane, a piston-type actuator, a sevo motor, and a mounting bracket, said servo motor being secured to said mounting bracket, said mounting bracket being secured to said housing, a first end of said piston-type actuator being engaged with said servo motor, a second end of said piston-type actuator being secured to said elastomeric membrane, said housing defining a chest cavity actuator opening proximate said chest cavity actuator assembly, said chest cavity actuator opening being covered by said elastomeric membrane, said servo motor being operated to reciprocate said second end of said piston-type actuator away from and toward said housing to draw air into and expel air from the donor lungs through the trachea.

3. The heart and lung support assembly of claim 1 wherein said blood pressure controller assembly includes a flexible tubing section carried within said fluid circuit, a piston-type actuator, a servo motor, and a mounting bracket, said servo motor being secured to said mounting bracket, said mounting bracket being secured to said housing, a first end of said piston-type actuator being engaged with said servo motor, a second end of said piston-type actuator being disposed in engagement with said flexible tubing section, said servo motor being operated to move said second end of said piston-type actuator toward and away from a center of said flexible tubing section to vary a cross-sectional area therein, thereby respectively increasing and decreasing the aortic blood pressure.

4. The heart and lung support assembly of claim 1 wherein said blood content detector is provided for detecting at least:

a partial pressure of oxygen ($pO_2$);

a partial pressure of carbon dioxide ($pCO_2$); and a pH level.

5. The heart and lung support assembly of claim 1 wherein said at least one blood pressure detector includes at least:

a central venous pressure detector, said central venous pressure detector being provided for measuring the blood pressure in the right auricle of the donor heart, a pulmonary artery pressure detector, said pulmonary artery pressure detector being provided for measuring the pressure of the venous blood going into the donor lungs from the right side of the donor heart;

a left auricle pressure detector, said left auricle pressure detector being provided for measuring the pressure in the left auricle of the donor heart; and an aortic pressure detector, said aortic pressure detector being provided for measuring the pressure of blood leaving the donor heart from the left ventricle thereof.

6. The heart and lung support assembly of claim 1 wherein said blood content detector of said automated monitor and feedback control system includes a comparator for comparing values measured by said blood content detector to normal values, a signal processor for determining whether said values measured by said blood content detector are within an acceptable range, and a controller for controlling said chest cavity actuator in response to said signal processor in order to vary an amount and rate of air drawn into and expelled from the donor lungs.

7. The heart and lung support assembly of claim 1 wherein said blood pressure detector of said automated monitor and feedback control system includes a comparator for comparing values measured by said at least one blood pressure detector to normal values, a signal processor for determining whether said values measured by said at least one blood pressure detector are within an acceptable range, and a controller for controlling said blood pressure controller assembly in response to said signal processor in order to vary the blood pressure between the left ventricle and the right auricle of the donor heart.

8. The heart and lung support assembly of claim 1 further comprising a pair of defibrillator pads carried by said housing for applying an electrical shock to the donor heart.

9. The heart and lung support assembly of claim 1 further comprising a pacemaker for controlling the heart rate of the donor heart within prescribed limits.

10. The heart and lung support assembly of claim 1 wherein said fluid circuit further includes a hemo filter for removing impurities from the blood circulated through said heart and lung support assembly.

11. A heart and lung support assembly for extracorporeal support of a donor heart using the donor lungs as an oxygenator for blood being pumped therethrough by the donor heart, said heart and lung support assembly comprising:

a housing defining an enclosure for placement of a donor heart and donor lungs, said housing defining a trachea opening configured to mount a trachea receptor therein, said trachea receptor being configured for attachment of a trachea associated with the donor lungs thereto;

a cradle carried within said housing above a bottom of said housing for placement of the donor heart thereon, the donor lungs being positioned on said housing bottom below the donor heart, the donor lungs remaining intact with and in a normal disposition with the donor heart;

a chest cavity actuator assembly carried by said housing for inducing inhaling and exhaling of the donor lungs, said chest cavity actuator being operable to create a vacuum within said housing to induce a draw of air into the donor lungs;

a fluid circuit for circulating blood through the donor heart and donor lungs in similar fashion to the circulatory system associated with the donor heart;

a blood pressure controller assembly for selectively raising and lowering the pressure of blood being pumped through said heart and lung support assembly; and an automated monitor and feedback control system including a blood content detector for detecting levels of components in blood circulated through said heart and lung support assembly and at least one blood pressure detector for detecting at least one blood pressure associated with the donor heart, said automated monitor and feedback control system controlling said chest cavity actuator assembly and said blood pressure controller assembly as a result of data obtained from said blood content detector and said at least one blood pressure detector, said blood content detector being provided for detecting at least:

a partial pressure of oxygen (pO$_2$);

a partial pressure of carbon dioxide (pCO$_2$); and a pH level, said plurality of blood pressure detectors including at least:

a central venous pressure detector, said central venous pressure detector being provided for measuring the blood pressure in the right auricle of the donor heart;

a pulmonary artery pressure detector, said pulmonary artery pressure detector being provided for measuring the pressure of the venous blood going into the donor lungs from the right side of the donor heart;

a left auricle pressure detector, said left auricle pressure detector being provided for measuring the pressure in the left auricle of the donor heart; and an aortic pressure detector, said aortic pressure detector being provided for measuring the pressure of blood leaving the donor heart from the left ventricle thereof.

12. The heart and lung support assembly of claim 11 wherein said chest cavity actuator assembly includes an elastomeric membrane, a piston-type actuator, a servo motor, and a mounting bracket, said servo motor being secured to said mounting bracket, said mounting bracket being secured to said housing, a first end of said piston-type actuator being engaged with said servo motor, a second end of said piston-type actuator being secured to said elastomeric membrane, said housing defining a chest cavity actuator opening proximate said chest cavity actuator assembly, said chest cavity actuator opening being covered by said elastomeric membrane, said servo motor being operated to reciprocate said second end of said piston-type actuator away from and toward said housing to draw air into and expel air from the donor lungs through the trachea.

13. The heart and lung support assembly of claim 11 wherein said blood pressure controller assembly includes a flexible tubing section carried within said fluid circuit, a piston-type actuator, a servo motor, and a mounting bracket, said servo motor being secured to said mounting bracket, said mounting bracket being secured to said housing, a first end of said piston-type actuator being engaged with said servo motor, a second end of said piston-type actuator being disposed in engagement with said flexible tubing section, said servo motor being operated to move said second end of said piston-type actuator toward and away from a center of said flexible tubing section to vary a cross-sectional area therein, thereby respectively increasing and decreasing the aortic blood pressure.

14. The heart and lung support assembly of claim 11 wherein said blood content detector of said automated monitor and feedback control system includes a comparator for comparing values measured by said at least one blood content detector to normal values, a signal processor for determining whether said values measured by said at least one blood content detector are within an acceptable range, and a controller for controlling said chest cavity actuator assembly in response to said signal processor in order to vary an amount and rate of air drawn into and expelled from the donor lungs.

15. The heart and lung support assembly of claim 11 wherein said blood pressure detector of said automated monitor and feedback control system includes a comparator for comparing values measured by said at least one blood pressure detector to normal values, a signal processor for determining whether said values measured by said at least one blood pressure detector are within an acceptable range, and a controller for controlling said blood pressure controller assembly in response to said signal processor in order to vary the blood pressure between the left ventricle and the right auricle of the donor heart.

16. The heart and lung support assembly of claim 11 further comprising a pair of defibrillator pads carried by said housing for applying an electrical shock to the donor heart.

17. The heart and lung support assembly of claim 11 further comprising a pacemaker for controlling the heart rate of the donor heart within prescribed limits.

18. A heart and lung support assembly for extracorporeal support of a donor heart using the donor lungs as an oxygenator for blood being pumped therethrough by the donor heart, said heart and lung support assembly comprising:

a housing defining an enclosure for placement of a donor heart and donor lungs, said housing defining a trachea opening configured to mount a trachea receptor therein, said trachea receptor being configured for attachment of a trachea associated with the donor lungs thereto, a cradle carried within said housing above a bottom of said housing for placement of the donor heart thereon, the donor lungs being positioned on said housing bottom below the donor heart, the donor lungs remaining intact with and in a normal disposition with the donor heart;

a chest cavity actuator assembly carried by said housing for inducing inhaling and exhaling of the donor lungs, said chest cavity actuator being operable to create a vacuum within said housing to induce a draw of air into the donor lungs, said chest cavity actuator assembly including an elastomeric membrane, a piston-type actuator, a servo motor, and a mounting bracket, said servo motor being secured to said mounting bracket, said mounting bracket being secured to said housing, a first end of said piston-type actuator being engaged with said servo motor, a second end of said piston-type actuator being secured to said elastomeric membrane, said housing defining a chest cavity actuator opening proximate said chest cavity actuator assembly and a trachea opening, said chest cavity actuator opening being covered by said elastomeric membrane, said trachea opening being configured to mount a trachea receptor therein, said servo motor being operated to reciprocate said second end of said piston-type actuator away from and toward said housing to draw air into and expel air from the donor lungs through the trachea;

a fluid circuit for circulating blood through the donor heart and donor lungs in similar fashion to the circulatory system associated with the donor heart;

a blood pressure controller assembly for selectively raising and lowering the pressure of blood being pumped through said heart and lung support assembly, said blood pressure controller assembly including a flexible tubing section carried within said fluid circuit, a piston-type actuator, a servo motor, and a mounting bracket, said servo motor being secured to said mounting bracket, said mounting bracket being secured to said housing, a first end of said piston-type actuator being engaged with said servo motor, a second end of said piston-type actuator being disposed in engagement with said flexible tubing section, said servo motor being operated to move said second end of said piston-type actuator toward and away from a center of said flexible tubing section to vary a cross-sectional area therein, thereby respectively increasing and decreasing the aortic blood pressure, and an automated monitor and feedback control system including a blood content detector for detecting levels of components in blood circulated through said heart and lung support assembly and at least one blood pressure detector for detecting at least one blood pressure associated with the donor heart, said automated monitor and feedback control system controlling said chest cavity actuator assembly and said blood pressure controller assembly as a result of data obtained from said blood content detector and said at least one blood pressure detector, said blood content detector being provided for detecting at least:

a partial pressure of oxygen ($pO_2$);

a partial pressure of carbon dioxide ($pCO_2$); and a pH level, said plurality of blood pressure detectors including at least:

a central venous pressure detector, said central venous pressure detector being provided for measuring the blood pressure in the right auricle of the donor heart;

a pulmonary artery pressure detector, said pulmonary artery pressure detector being provided for measuring the pressure of the venous blood going into the donor lungs from the right side of the donor heart;

a left auricle pressure detector, said left auricle pressure detector being provided for measuring the pressure in the left auricle of the donor heart; and an aortic pressure detector, said aortic pressure detector being provided for measuring the pressure of blood leaving the donor heart from the left ventricle thereof, said blood content detector of said automated monitor and feedback control system further including a first comparator for comparing values measured by said blood content detector to normal values, a first signal processor for determining whether said values measured by said blood content detector are within an acceptable range, and a first controller for controlling said chest cavity actuator assembly in response to said first signal processor in order to vary an amount and rate of air drawn into and expelled from the donor lungs, said automated monitor and feedback control system further including a second comparator for comparing values measured by said plurality of blood pressure detectors to normal values, a second signal processor for determining whether said values measured by said plurality of blood pressure detectors are within an acceptable range, and a second controller for controlling said blood pressure controller assembly in response to said second signal processor in order to vary the blood pressure between the left ventricle and the right auricle of the donor heart.

19. The heart and lung support assembly of claim 18 further comprising a pair of defibrillator pads carried by said housing for applying an electrical shock to the donor heart.

20. The heart and lung support assembly of claim 18 further comprising a pacemaker for controlling the heart rate of the donor heart within prescribed limits.

* * * * *